United States Patent [19]
Petrovic et al.

[11] Patent Number: 6,107,433
[45] Date of Patent: Aug. 22, 2000

[54] PROCESS FOR THE PREPARATION OF VEGETABLE OIL-BASED POLYOLS AND ELECTRONINSULATING CASTING COMPOUNDS CREATED FROM VEGETABLE OIL-BASED POLYOLS

[75] Inventors: Zoran Petrovic; Andrew Guo; Ivan Javni, all of Pittsburg, Kans.

[73] Assignee: Pittsburg State University, Pittsburg, Kans.

[21] Appl. No.: 09/187,992

[22] Filed: Nov. 6, 1998

[51] Int. Cl.$^7$ .................. C08G 83/00; C07D 303/00; C07D 301/14; C07D 301/19; C07D 301/00
[52] U.S. Cl. .................. 528/1; 549/513; 549/525; 549/530; 549/539
[58] Field of Search .................. 549/525, 513, 549/530, 539; 528/1

[56] References Cited

U.S. PATENT DOCUMENTS

| | | |
|---|---|---|
| 4,508,853 | 4/1985 | Kluth et al. . |
| 4,546,120 | 10/1985 | Peerman et al. . |
| 4,551,517 | 11/1985 | Herold et al. . |
| 4,742,087 | 5/1988 | Kluth et al. . |
| 4,826,944 | 5/1989 | Hoefer et al. . |
| 4,886,893 | 12/1989 | Meffert et al. . |
| 5,026,881 | 6/1991 | Gruber . |
| 5,266,714 | 11/1993 | Stoll et al. . |
| 5,302,626 | 4/1994 | Hoefer et al. . |

FOREIGN PATENT DOCUMENTS

| | | |
|---|---|---|
| 39 43 080 | 7/1991 | Germany . |
| 41 15 146 | 11/1992 | Germany . |
| 41 28 649 | 3/1993 | Germany . |

OTHER PUBLICATIONS

Scholnick et al., "Urethane Foams from Animal Fats. IV. Rigid Foams from Epoxidized Glycerides," *Journal of the American Oil Chemists' Society*, vol. 45, pp. 76–77, 1968.

*Primary Examiner*—Patrick D. Niland
*Attorney, Agent, or Firm*—Shook, Hardy & Bacon LLP

[57] ABSTRACT

A vegetable oil-based polyol is made by adding a peroxyacid to vegetable oil wherein said peroxyacid reacts with said vegetable oil to form epoxidized vegetable oil and adding said epoxidized vegetable oil to a mixture of an alcohol, water, and a catalytic amount of fluoboric acid so as to form a vegetable oil-based polyol. A further embodiment of the present invention involves making a vegetable oil-based polyol using an epoxidized vegetable oil as the starting material. The epoxidized vegetable oil undergoes hydroxylation by the same process as outlined above. According to another aspect of the present invention, the vegetable oil-based polyol formed by the novel methods of this invention may be reacted with an isocyanate to form a polyurethane. Alternatively, a filler such as silica may be combined with the vegetable oil-based polyol before it is reacted with the isocyanate. These polyurethanes made from vegetable oil-based polyols may be used to form electroinsulating casting resins.

11 Claims, No Drawings

PROCESS FOR THE PREPARATION OF VEGETABLE OIL-BASED POLYOLS AND ELECTROINSULATING CASTING COMPOUNDS CREATED FROM VEGETABLE OIL-BASED POLYOLS

STATEMENT REGARDING FEDERALLY-SPONSORED RESEARCH OR DEVELOPMENT

Not applicable.

CROSS REFERENCE TO RELATED APPLICATIONS

Not applicable.

BACKGROUND OF THE INVENTION

The present invention relates to a method for making vegetable oil-based polyols. Still further, the present invention includes using vegetable oil-based polyols to produce polyurethane resins for use as casting compounds for electrical applications.

Polyols may be produced from petroleum. However, vegetable oils come from renewable resources. Vegetable oil molecules must be chemically transformed in order to introduce hydroxyl groups. For instance, soybean oil does not contain any hydroxyl groups but has on an average about 4.6 double bonds per molecule. The unsaturated portions of the vegetable oil molecule can be converted to hydroxyl groups. However, many reactions for preparing polyols from vegetable oils are not very selective. By-products, in addition to alcohol groups, are created during the transformation. Furthermore, many conventional methods of preparing polyols from vegetable oil do not produce polyols having a significant content of hydroxyl groups. Still further, many available methods of preparing polyols from vegetable oils do not produce products having a desirable viscosity. Greases or waxes often result as a consequence of such chemical transformations.

Conventionally, cast electrical components such as dry voltage transformers and insulators are formed from epoxy resins. Epoxy resins are rather expensive to use. Still further, epoxy resins are not easy to handle at low temperatures and have poor elasticity. Polyurethane resins prepared with castor oil have also been produced. However, these resins tend to be rubbery and thus undesirable for certain casting applications. Still further, castor oil-based polyurethanes have some limitations due to their higher price and environmental problems related to their by-products.

In order to overcome the deficiencies found with conventional processes for making vegetable oil-based polyols, a method for making vegetable oil-based polyols from vegetable oil or epoxidized vegetable oil is needed for a variety of applications including preparation of, through polyurethane chemistry, a resin for use as an electroinsulating casting compound, which is another embodiment of the present invention. Still further, this method of making vegetable oil-based polyols should avoid substantial side-reactions, such as esterification, cyclization, polymerization, and other undesirable reactions, and should produce polyols having a high hydroxyl content and a desirable viscosity.

SUMMARY OF THE INVENTION

It is an object of the present invention to provide a method for making polyols from renewable resources.

It is another object of the present invention to provide a method for making vegetable oil-based polyols directly from vegetable oil in a continuous two-step process so that unnecessary intermediate steps are avoided.

Another object of the present invention is to provide polyurethane resins made from vegetable oil-based polyols and methods for making the same in order to create polyurethane casting compounds having improved hydrolytic properties and improved thermal stability.

Still another object of the present invention is to provide a method for making vegetable oil-based polyols having a desirable viscosity and a high content of hydroxyl groups.

A further object of the present invention is to provide a casting resin made from vegetable oil-based polyols having improved mechanical and dielectric properties over conventional casting resins and a method for making the same so that a casting compound having excellent insulating properties and durability may be provided.

Still another object of the present invention is to provide a method for making vegetable oil-based polyols having a favorable distribution of hydroxyl groups in the molecule so that when these polyols are reacted with isocyanates to form polyurethanes, crosslinking within the polyurethane is optimized.

Still another object of the present invention is to provide a method for making various vegetable oil-based polyols having a range of hydroxyl content so that cast polyurethane materials having a range of glass transition characteristics may be created. Depending upon the type of vegetable oils used as the starting material, polyurethane resins ranging from soft rubber to rigid plastics may be created.

According to the present invention, the foregoing and other objects are achieved by a method for making vegetable oil-based polyols directly from vegetable oil using a consecutive two-step process involving epoxidation and hydroxylation. Specifically, this process comprises adding a peroxyacid to vegetable oil wherein said vegetable oil and said peroxyacid react to form epoxidized vegetable oil and adding said epoxidized vegetable oil to a mixture of an alcohol, water, and a fluoboric acid catalyst wherein the epoxidized vegetable oil undergoes hydroxylation so as to form a vegetable oil-based polyol.

The vegetable oil-based polyols created by this method may be reacted with isocyanates so as to form polyurethanes, which is another embodiment of the present invention. Alternatively, fillers such as silica may be combined with these vegetable oil-based polyols before they are reacted with isocyanates to form polyurethanes. In still another embodiment of the present invention, polyurethanes made from vegetable oil-based polyols may be used to form electroinsulating casting resins for use in electrical applications.

Additional objects, advantages and novel features of the invention will be set forth in part in the description which follows, and in part will become apparent to those skilled in the art upon examination of the following, or may be learned from practice of the invention. The objects and advantages of the invention may be realized and attained by means of the instrumentalities and combinations particularly pointed out in the appended claims.

DETAILED DESCRIPTION OF THE PREFERRED EMBODIMENT

The method of the present invention involves making vegetable oil-based polyols by converting each of the double bonds of the vegetable oil molecule into a hydroxyl group. This method takes place at approximately atmospheric pressure.

The process of the present invention involves epoxidation and subsequent hydroxylation of vegetable oil so as to make a polyol. More specifically, the process of the present invention includes adding a peroxyacid in a solvent to vegetable oil wherein said vegetable oil and said peroxyacid react to form epoxidized vegetable oil, and adding said epoxidized vegetable oil, which is in the solvent, to a mixture of an alcohol, water, and a catalytic amount of fluoboric acid so as to form a vegetable oil-based polyol. These are consecutive, non-stop steps. The reaction is not stopped after the epoxidized vegetable oil forms so as to purify the intermediate product.

Any vegetable oil may be used in this process. Examples of vegetable oils that may be used include, but are not limited to, soybean oil, safflower oil, linseed oil, corn oil, sunflower oil, olive oil, canola oil, sesame oil, cottonseed oil, palm oil, rapeseed oil, tung oil, fish oil, or a blend of any of these oils. Alternatively, any partially hydrogenated vegetable oils or genetically modified vegetable oils can be used to obtain the desired hydroxyl content. Examples of partially hydrogenated vegetable oils or genetically modified vegetable oils include, but are not limited to, high oleic safflower oil, high oleic soybean oil, high oleic peanut oil, high oleic sunflower oil and high erucic rapeseed oil (crambe oil). The iodine values of these vegetable oils range from about 40 to 240 and more preferably from about 80 to 240. When vegetable oils having lower iodine values are used to make vegetable oil-based polyols, polyols with lower hydroxyl numbers and thus lower viscosities are created.

Any peroxyacid may be used in the epoxidation reaction. Examples of peroxyacids that may be used include, but are not limited to, peroxyformic acid, peroxyacetic acid, trifluoroperoxyacetic acid, benzyloxyperoxyformic acid, 3,5-dinitroperoxybenzoic acid, m-chloroperoxybenzoic acid, or any combination of these peroxyacids. The peroxyacids may be formed in-situ by reacting a hydroperoxide with the corresponding acid, such as formic or acetic acid. Examples of hydroperoxides that may be used include, but are not limited to, hydrogen peroxide, tert-butylhydroperoxide, triphenylsilylhydroperoxide, cumylhydroperoxide, or any combination of these hydroperoxides. Preferably, the peroxyacid is in a solvent such as acetic acid, formic acid, or chloroform.

Fluoboric acid is used as the acid catalyst in the hydroxylation step. Using fluoboric acid as a catalyst in this hydroxylation reaction works better than using other inorganic acids suggested by the prior art. Specifically, by using fluoboric acid, the vegetable oil-based polyol produced consistently has a higher hydroxyl content. A catalytic amount of fluoboric acid is used in this reaction, which should be about 2% or less by weight of the amount of epoxidized vegetable oil used.

Examples of alcohols or alcohol mixtures that may be used in the hydroxylation reaction include, but are not limited to, monoalcohols such as methanol, ethanol, propanol, and butanol. It is desirable to have methanol be part of the alcohol mixture used in the hydroxylation reaction because it is the most reactive alcohol. However, if methanol is used alone, undesired cleavages of the triglyceride occur. Preferably, the alcohol used in the hydroxylation reaction is a mixture of methanol and isopropanol. Other alcohol mixtures may also be used so long as the methanol concentration is kept low. In fact, methanol may be used with solvents other than alcohols, such as chloroform, toluene, formic acid, or acetic acid. It is important during the hydroxylation step to always have an excess amount of alcohol present so as to prevent polymerization and the formation of products having higher viscosities.

Water is also an important component in this reaction. It reacts with the epoxy groups of the epoxidized vegetable oils to form two hydroxyl groups per epoxy group in some location so as to increase the hydroxyl content of the vegetable oil-based polyols. Specifically, water contributes to about 10% or lower dihydroxylation of the vegetable oil. Still further, it acts as a diluent to the fluoboric acid so that the acid is not reactive towards undesired cleavage of the triglyceride linkages present in the vegetable oil molecules.

The molar ratio of water to epoxy groups is from about 1:1 to about 10:1. In a preferred embodiment of the present invention, where a mixture of methanol and isopropanol is used as the alcohol in the hydroxylation reaction, the molar ratio of methanol to epoxy groups is from about 1:1 to about 10:1 and preferably is about 4:1 to about 10:1. The molar ratio of isopropanol to epoxy groups is from about 5:1 to about 10:1 and preferably is about 8:1.

The epoxidation reaction occurs at approximately room temperature or between about 20 and 30° C. During the hydroxylation step, the temperature rises. The extent to which the temperature rises depends upon the amount of solvent present. If the temperature rises to less than 50° C., it is preferable to increase the reaction speed by warming the reaction mixture to this temperature.

The vegetable oil-based polyols made by the method of the present invention have a viscosity in the range of 1,000–7,000 centipoise at room temperature. The viscosity of these polyols is lower than vegetable oil-based polyols made by other methods because the method of the present invention avoids substantial side-reactions, such as polymerization or crosslinking. Still further, the vegetable oil-based polyols made by the method of the present invention have a hydroxyl content ranging from 110 to 213 mg KOH/g. Preferably, the polyol has a high hydroxyl content which equals to approximately one hydroxyl group per double bond of the vegetable oil. Vegetable oil-based polyols can be made in yields of 85–95% using any of the various embodiments of the process of the present invention.

This method for making vegetable oil-based polyols is illustrated in the following examples. These examples are not meant in any way to limit the scope of this invention.

EXAMPLE 1

A soy polyol was created from soybean oil by using peracetic acid in the epoxidation step and acetic acid as the solvent. First, 19 grams of soybean oil were placed in a 500-milliliter three-necked flask equipped with a thermometer, a drop funnel, and a magnetic stirrer. 12 grams of pre-prepared solution of peracetic acid in acetic acid (~1 Molar) were added dropwise over 10 minutes to the oil while the temperature of the mixture was maintained at 10° C. by an ice-water bath. The mixture was stirred at 20–25° C. for another 5 hours, and a solution of epoxidized soybean oil in acetic acid was obtained. 30 milliliters of methanol and 1 gram of fluoboric acid (48% in water) were placed in a second 500-milliliter flask. The afore-prepared epoxidized soybean oil solution was added dropwise to the methanol/fluoboric acid solution at room temperature over 15 minutes, by which time the temperature of the mixture had reached 43° C. The mixture was stirred at 50° C. for another hour. After the flask was cooled to room temperature, 200 milliliters of water and 100 milliliters of chloroform were added to the flask and the organic phase was separated. It was then washed with 50 milliliters of water until a neutral pH was obtained. It was dried over magnesium sulfate and filtered. The solvent was removed under vacuum, and a yellow oily liquid was obtained. The product was found to have a hydroxyl value of 169 mg KOH/g and a viscosity of 6,800 centipoise at 30° C.

EXAMPLE 2

A soy polyol was created from soybean oil by using m-chloroperoxybenzoic acid in the epoxidation step and chloroform was used as the solvent. First, 19 grams of soybean oil were dissolved in 50 milliliters of chloroform in a 250-milliliter three-necked flask equipped with a thermometer, a drop fennel, and a magnetic stirrer. A solution of 28 grams of m-chloroperoxybenzoic acid in 100 milliliters of chloroform was added dropwise over 20 minutes to the oil while the temperature of the mixture was maintained at 10° C. by an ice-water bath. The mixture was stirred at room temperature for another 2 hours and then filtered. A solution of epoxidized soybean oil in chloroform is thus obtained. 40 milliliters of methanol, 1.8 grams of water and 1 gram of fluoboric acid (48% in water) were placed in a second 250-milliliter flask. The afore-prepared epoxidized soybean oil solution was added dropwise at 40° C. over 15 minutes, by which time the temperature of the mixture had reached 50° C. The mixture was stirred at 50° C. for another hour. After the flask was cooled to room temperature, 200 milliliters of water were added to the flask and the organic phase was separated. It was then washed sequentially twice with 50 milliliters of water, once with 50 milliliters of sodium bicarbonate solution (5%), twice with 50 milliliters of water, and once with 50 milliliters of saline solution. It was dried over magnesium sulfate and filtered. The solvent was removed under vacuum, and a yellow oily liquid was obtained. The product was found to have a hydroxyl value of 213 mg KOH/g and a viscosity of 3,800 centipoise at 30° C.

EXAMPLE 3

A safflower oil polyol was created from safflower oil by using m-chloroperoxybenzoic acid in the epoxidation step and chloroform was used as the solvent. While stirring, 100 grams of safflower oil and 200 milliliters of chloroform were added into a 2-liter three-necked flask equipped with a mechanical stirrer, a thermometer, and a pour funnel. 148 grams of m-chloroperoxybenzoic acid (73%) in 500 milliliters of chloroform were added to the safflower oil mixture slowly through the pour funnel over a period of 30 minutes, and the reaction temperature was controlled at around 10° C. by an ice-water bath. The flask was allowed to warm to room temperature and the stirring was continued for two hours. The epoxidized safflower oil was vacuum filtered using a 100-milliliter vacuum flask and a 350-milliliter sintered glass funnel. 50 milliliters of chloroform were used to rinse the precipitate.

200 milliliters of methanol and 5 grams of fluoboric acid were added into a 2-liter three-necked flask equipped with a mechanical stirrer, a condenser and an additional funnel while stirring. After the content of the flask was warmed to 40° C. by a heated water bath, the afore-prepared epoxidized safflower oil was added to the flask over a period of 15 minutes. The reaction mixture continued to be stirred at 40–50° C. for one additional hour. After the flask was cooled to room temperature, 500 milliliters of water were added to the flask and the organic phase was separated. It was then washed sequentially, twice with 200 milliliters of water, once with 200 milliliters of ammonia solution (5%), twice with 200 milliliters of water, and once with 200 milliliters of saline solution. It was dried over magnesium sulfate and filtered. The solvent was removed under vacuum, and a yellow oily liquid was obtained. The product was found to have a hydroxyl value of 180 mg KOH/g and a viscosity of 4,200 centipoise at 30° C.

EXAMPLE 4

A sunflower polyol was created from sunflower oil by using m-chloroperoxybenzoic acid in the epoxidation step, and chloroform was used as the solvent. The procedure used was the same as illustrated in Example 3, and the sunflower polyol obtained was a yellow oily liquid. The product was found to have a hydroxyl value of 161 mg KOHI/g and a viscosity of 4,800 centipoise at 30° C.

EXAMPLE 5

A canola polyol was created from canola oil by using m-chloroperoxybenzoic acid in the epoxidation step, and chloroform was used as the solvent. The procedure used was the same as illustrated in Example 3, and the canola polyol obtained was a yellow oily liquid. The product was found to have a hydroxyl value of 144 mg KOH/g and a viscosity of 1,000 centipoise at 30° C.

EXAMPLE 6

A corn polyol was created from corn oil by using m-chloroperoxybenzoic acid in the epoxidation step, and chloroform was used as the solvent. The procedure used was the same as illustrated in Example 3, and the canola polyol obtained was an orange oily liquid. The product was found to have a hydroxyl value of 140 mg KOH/g and a viscosity of 1,900 centipoise at 30° C.

EXAMPLE 7

An olive polyol was created from olive oil by using m-chloroperoxybenzoic acid in the epoxidation step, and chloroform was used as the solvent. The procedure used was the same as illustrated in Example 3, and the olive polyol obtained was a yellow oily liquid. The product was found to have a hydroxyl value of 138 mg KOH/g and a viscosity of 840 centipoise at 30° C.

EXAMPLE 8

A peanut polyol was created from peanut oil using m-chloroperoxybenzoic acid in the epoxidation step, and chloroform was used as the solvent. The procedure used was the same as illustrated in Example 3, and the peanut polyol was obtained as a yellow oily liquid. The product was found to have a hydroxyl value of 111 mg KOH/g and a viscosity of 1,200 centipoise at 30° C.

Still further, in another embodiment of the present invention, epoxidized vegetable oils may be used as a starting material and only the second step of the process discussed above, the hydroxylation step, is implemented. Specifically, this embodiment involves hydroxylating epoxidized vegetable oil with an alcohol, water, and a catalytic amount of fluoboric acid to form a vegetable oil-based polyol. Preferably, the amounts of components and the conditions of the reaction are the same as outlined above. Preferably, the epoxidized vegetable oil is added to the alcohol, water, and catalyst mixture in performing this hydroxylation step.

Epoxidized vegetable oils may be prepared in conventional ways well defined in the prior art such as in the J. Am. Chem. Soc., Volume 67, pages 412–414 (1945) and U.S. Pat. No. 4,647,678 or may be obtained from commercial sources.

In the case of epoxidized soybean oil, it may be obtained from Union Carbide (Taft Plant, P.O. Box 50, Hahnville, La. 70057), Ferro Corporation (Polymer Additives Division, 7050 Krick Road, Walton Hills, Ohio 44146), C. P. Hall Co. (31 1 S. Wacker Dr., Suite 4700, Chicago, Ill. 60606), or Ashland Chemical Co. (P.O.Box 2219, Columbus, Ohio 43216). Preferably, the epoxidized vegetable oil used in this embodiment of the method of the present invention has an epoxide content of about 2–8 weight %. In other terms, preferably, each epoxidized vegetable oil molecule has about 2 to 6 epoxy groups.

The vegetable oil-based polyol created by this alternate embodiment of the present invention has similar characteristics to the polyol created by the previous embodiment of the present invention.

The following are examples of methods of making vegetable oil-based polyols, according to the present invention, using epoxidized soybean oil as a starting material. These examples are not meant in any way to limit the scope of this invention.

EXAMPLE 9

A soy polyol was created from epoxidized soybean oil FLEXOL® from Union Carbide (Taft Plant, P.O. Box 50, Hahnville, La. 70057). FLEXOL® Plasticizer EPO has an epoxide content of 7. 1% by weight, an iodine number of 1.0, an acid number of 0.2 mg KOH/g, a hydroxyl value of 5 mg KOH/g, a viscosity at 100° F of 188 centistokes, a specific gravity at 25° C. of 0.992, a platinum-cobalt color of 61, and an appearance that is free of suspended matter.

First, 700 milliliters of methanol, 2.7 liters of isopropanol, 100 milliliters of water, and 45 grams of fluoboric acid (48% in water) were mixed at room temperature in a 5-liter two-necked flask equipped with a condenser, a thermometer and a magnetic stirrer. 940 grams of epoxidized soybean oil were added through the condenser over a period of 30 minutes, by which time the temperature of the mixture had reached 55° C. and then started to decrease. The reaction was terminated 30 minutes later by adding sodium bicarbonate. The solvents were removed on a rotavapor, and 1 liter of toluene was added to the collected oily liquid. The mixture was then transferred to separatory funnels, washed sequentially twice with 500 milliliters of water, once with 500 milliliters of sodium bicarbonate solution (5%), twice with 500 milliliters of water, and once with 500 milliliters of saline solution. The organic phase was combined, dried over magnesium sulfate, and filtered. The solvent was removed under vacuum, and a yellowish viscous liquid was obtained in nearly quantitative yield. The product was found to have a hydroxyl value of 184 mg KOH/g and a viscosity of 7,200 centipoise at 30° C.

EXAMPLE 10

A soy polyol was created from epoxidized oil PLAS-CHEK® 775 from Ferro Corporation (Polymer Additives Division, 7050 Krick Road, Walton Hills, Ohio 44146). PLAS-CHEK® 775 has an epoxide content of 7.0% by weight, an iodine number of 1.2, an acid number of 0.3 mg KOH/g, a refractive index of 1.472, a Gardner viscosity of N, a specific gravity at 25° C. of 0.992, and a APHA color of 110. The procedure used was the same as illustrated in Example 9, and the soy polyol was obtained as a yellow oily liquid. The product was found to have a hydroxyl value of 215 mg KOH/g and a viscosity of 10,400 centipoise at 30° C.

In another embodiment of the present invention, the vegetable oil-based polyols created by the method of the present invention or by other methods may be reacted with isocyanates to form polyurethanes. The vegetable oil-based polyols produced by the present invention have a range of hydroxyl content varying from 110 to 213 mg KOH/g, which will lead to polyurethane materials having a range of physical and mechanical properties, suitable for a variety of applications.

Alternatively, a filler may be added to the vegetable oil-based polyol before it is reacted with the isocyanate. Examples of fillers that may be added include, but are not limited to, silica, alumina, calcium carbonate, dolomite, silicates, glass, ceramic, sand, clay, and talc. The filler may be combined with the vegetable oil-based polyol in about I to 200% by weight of the vegetable oil-based polyol. High modulus fillers such as silica and alumina may be abrasive if applied with machines requiring pumping, but they impart high electrical properties and excellent mechanical properties. Soft fillers like calcium carbonate give excellent flow properties and are more suitable for machine application. Using large quantities of fillers improves the thermal conductivity of the products created so that excellent dielectric strength may be provided.

One of the problems with using urethanes for electrical insulation is caused by the reaction of isocyanates with water, resulting in carbon dioxide gas formation and foaming. However, new moisture scavengers have been developed which react with water before it reacts with the isocyanate, allowing polyurethanes to be used in the electrical insulation field. Conventional moisture scavengers may be used in making the polyurethanes of the present invention.

In forming the polyurethane, the isocyanate reacts with the hydroxyl groups of the vegetable oil-based polyol. The vegetable oil-based polyol and the isocyanate are combined in approximately stoichiometric quantities. It is acceptable to use up to about 10% in excess of the stoichiometric quantity of either of these components. Examples of isocyanates that can be used include, but are not limited to, polymeric or crude diphenylmethane diisocyanate (MDI), modified MDI including hydrogenated MDI (HMDI), isophorone diisocyanate, and 2,4-toluene diisocyanate (TDI). PAPI 2901, available from Dow Chemicals, Midland, Mich. 48674, is an example of a polymeric or crude MDI that may be used. Isonate 2143 L, available from Dow Chemicals, is an example of a non-polymeric MDI that may be used. HMDI is a hydrogenated MDI, which is non-aromatic and can be used where light stability, arc and tracking resistance are required. The selection of the isocyanate component affects the crosslinking of the polyurethane.

Still further, a drying agent or an antifoaming agent may be added to the polyurethane, as desired. A drying agent is recommended because polyurethanes are very sensitive to moisture. An example of a drying agent that may be used is a zeolite paste such as Baylith L Paste, which is comprised of a 50% dispersion of zeolite in castor oil and may be obtained from Bayer Corp., 100 Bayer Road, Pittsburgh, Pa. 15205. In fact, a zeolite drying agent is the most preferred drying agent for polyurethane reactions. Additives such as pigments may also be added in forming the polyurethane.

The polyol and the filler should both be dried before being mixed together. The polyol, the filler and the other optional additives should then be mixed while the polyol and the filler are still hot so as to form a polyol component. The polyol component is mixed under vacuum conditions at about 40–60° C. for about 5 minutes or until foaming stops. This removes trapped air. Next, an approximately stoichiometric amount of an isocyanate is added. The isocyanate is stirred with the polyol component under nitrogen for about 2 minutes and then under vacuum for about 5 minutes at about 60° C. until foaming stops. The mixture of the polyol with the isocyanate can be poured into a mold under nitrogen and then heated at about 110° C. for about 24 hours to complete the reaction.

The polyurethane resins of the present invention can be cured at room temperature, although higher temperatures accelerate the curing process thus avoiding the use of a catalyst. At higher curing temperatures, the viscosity of the polyurethane is reduced and thus, gas evacuation from the compound is facilitated. This gives a higher degree of curing, which results in a final product having a higher glass transition point.

Polyurethane compounds based on vegetable oil-based polyols have higher thermal stability both in air and nitrogen have excellent electrical properties. Polyurethanes made from soybean oil and safflower oil polyols are more rigid, have better mechanical and electrical properties, and have better thermal resistance because of their higher transition temperature than polyurethanes made from other vegetable oil-based polyols. Specifically, they have higher strength and lower dielectric permitivity and loss factor at room temperature because of their higher glass transition temperature. Still further, polyurethanes made from soy and safflower polyols have more crosslinking and thus are denser than polyurethanes made from other vegetable oil-based polyols. The addition of a filler improves both mechanical strength and dielectric strength of all these polyurethanes made from vegetable oil-based polyols. Various mechanical and electrical properties of polyurethanes made from soybean oil-based polyols that contain varying amounts of filler are shown in the following table:

| FILLER, % | GLASS TRANSITION TEMP., Tg, ° C. | | PERMITTIVITY | $\epsilon''/\epsilon'$ | SURFACE RESISTIVITY | VOLUME RESISTIVITY | AVERAGE DIELECTRIC STRENGTH |
|---|---|---|---|---|---|---|---|
| $SiO_2$ | DMTA | TMA | $\epsilon'$ | tan δ | ohm | ohm.cm | KV/mm |
| 0 (Isonate) | 66 | 55 | 3.1 | 0.004 | 5.37E+15 | 1.69E+16 | 19.5 |
| 150 (Isonate) | 75 | 63 | 3.49 | 0.003 | 1.98E+15 | 9.41E+15 | 19.7 |
| 200 (Isonate) | 73 | 68 | — | — | — | — | — |
| 0 (PAPI) | 67 | 62 | 3.18 | 0.005 | 5.37E+15 | 1.72E+16 | 17.8 |
| 150 (PAPI) | 74 | 66 | 3.5 | 0.003 | 1.98E+15 | 1.73E+16 | 20.6 |
| 200 (PAPI) | 80 | 63 | 3.61 | 0.0029 | 1.98E+15 | 9.26E+15 | 19.7 | than corresponding polyurethane compounds based on polypropylene oxide (PPO) polyols, which are sometimes used in electroinsulation. Vegetable oil-based urethane compounds have better hydrolytic stability and lower absorption of water than corresponding PPO-based compound. Still further, vegetable oil-based polyurethane compounds have several orders higher bulk and surface resistivity than amine or anhydride cured epoxy resins.

Polyurethane casting resins based on vegetable oil-based polyols are relatively low viscosity systems. Thus, they are suitable for impregnation of electrocoils, and when filled, they are useful as casting insulators, dry transformers, and other various electrical components, which is another embodiment of the present invention. Polyurethanes made from vegetable oil-based polyols can be cast into various electrical components by pouring the polyol and isocyanate mixture into a mold. Typically, these compounds are used in mid-voltage insulating applications (up to 35 kV), such as cable connectors and dry transformers as well as in electronic industry for encapsulation, potting, embedding and casting. The products formed with polyurethane made from vegetable oil-based polyols can be rigid or elastic depending on customer needs. These products may also be used in non-electrical applications where excellent mechanical and chemical properties as well as machinability, hydrophobicity, colorability and economy are factors. Additional factors that make these products useful for a variety of applications are the fact that they are easy to process even at low temperatures and the fact that the hardness of the products created can be varied by changing component ratios.

The appearance of the polyurethane materials created from vegetable oil-based polyols ranges from rigid plastics to soft rubber at room temperature. These polyurethanes The following are examples of polyurethanes that may be created using vegetable oil-based polyols without using a filler. These examples are not meant in any way to limit the scope of this invention.

EXAMPLE 11

A cast polyurethane resin was made using 60 parts of soy polyol, the product of Example 9, 29 parts of Isonate 2143L, and 0.6 part of antifoaming agent. The soy polyol and the antifoaming agent were mixed together to form a polyol component. This polyol component was dried for 20 hours at 110° C. Next, Isonate 2143L was added at 60° C. The polyol and the isocyanate components were stirred under nitrogen for two minutes and then under vacuum for five minutes at 60° C. until the foaming stopped. The mixture was then poured into a mold under nitrogen and the unit was left under vacuum to evacuate bubbles (5 minutes at 60° C.) and then the vacuum was removed. The sample was baked for 24 hours at 110° C. to complete the reaction. The sample was then cooled to room temperature and demolded. This cast polyurethane resin appeared as a rigid plastic having a glass transition temperature of 58° C. The cast resin may be molded into electroinsulating components.

EXAMPLE 12

A cast polyurethane resin was made using 40 parts of soy polyol, the product of Example 10, and 23 parts of Isonate 2143L without using any drying agent, antifoaming agent, or filler. The polyol was dried for 20 hours at 110° C. Next, Isonate 2143L was added at 60° C. The polyol and the isocyanate components were stirred under nitrogen for two minutes and then under vacuum for five minutes at 60° C. until the foaming stopped. The mixture was then poured into a mold under nitrogen and the unit was left under vacuum to evacuate bubbles (5 minutes at 60° C.) and then the vacuum was removed. The sample was baked for 24 hours at 110° C. to complete the reaction. The sample was then cooled to room temperature and demolded. This cast polyurethane resin appeared as a rigid plastic having a glass transition temperature of 75° C. The cast resin may be molded into electroinsulating components.

EXAMPLE 13

A cast polyurethane resin was made from 60 parts of soy polyol, the product of Example 9, 27 parts of PAPI 2901, 3 parts of drying agent, and 0.6 parts antifoaming agent. The soy polyol, the drying agent and the antifoaming agent were mixed together to form a polyol component. This polyol component was dried for 20 hours at 110° C. Next, PAPI 2901 was added at 60° C. The polyol and the isocyanate components were stirred under nitrogen for two minutes and then under vacuum for five minutes at 60° C. until the foaming stopped. The mixture was then poured into a mold under nitrogen and the unit was left under vacuum to evacuate bubbles (5 minutes at 60° C.) and then the vacuum was removed. The sample was baked for 24 hours at 110° C. to complete the reaction. The sample was then cooled to room temperature and demolded. This cast polyurethane resin appeared as a rigid plastic having a glass transition temperature of 62° C. The cast resin may be molded into electroinsulating components.

EXAMPLE 14

A cast polyurethane resin was created using 20 parts of safflower polyol, the product of Example 3, and 9.4 parts of Isonate 2143L without using any drying agent, antifoaming agent, or filler. The procedures used were the same as illustrated in Example 12. This cast polyurethane resin appeared as a rigid plastic having a glass transition temperature of 48° C. The cast resin may be molded into electroinsulating components.

EXAMPLE 15

A cast polyurethane resin was created using 20 parts of sunflower polyol, the product of Example 4, and 8.4 parts of Isonate 2143L without using any drying agent, antifoaming agent, or filler. The procedures used were the same as illustrated in Example 12. This cast polyurethane resin appeared as a semi-rigid plastic having a glass transition temperature of 33° C. The cast resin may be molded into electroinsulating components.

EXAMPLE 16

A cast polyurethane resin was created using 20 parts of canola polyol, the product of Example 5, and 7.6 parts of Isonate 2143L without using any drying agent, antifoaming agent, or filler. The procedures used were the same as illustrated in Example 12. This cast polyurethane resin appeared as a semi-rigid plastic having a glass transition temperature of 26° C. The cast resin may be molded into electroinsulating components.

EXAMPLE 17

A cast polyurethane resin was created using 20 parts of corn polyol, the product of Example 6, and 7.4 parts of Isonate 2143L without using any drying agent, antifoaming agent, or filler. The procedures used were the same as illustrated in Example 12. This cast polyurethane resin appeared as a semi-soft rubber having a glass transition temperature of 15° C. The cast resin may be molded into electroinsulating components.

EXAMPLE 18

A cast polyurethane resin was created using 20 parts of olive polyol, the product of Example 7, and 7.2 parts of Isonate 2143L without using any drying agent, antifoaming agent, or filler. The procedures used were the same as illustrated in Example 12. This cast polyurethane resin appeared as a semi-soft rubber having a glass transition temperature of 1 5° C. The cast resin may be molded into electroinsulating components.

EXAMPLE 19

A cast polyurethane resin was created using 20 parts of peanut polyol, the product of Example 8, and 5.8 parts of Isonate 2143L without using any drying agent, antifoaming agent, or filler. The procedures used were the same as illustrated in Example 12. This cast polyurethane resin appeared as a soft rubber having a glass transition temperature of 3° C. The cast resin may be molded into electroinsulating components.

The following are examples of polyurethane materials that may be created using the aforementioned vegetable oil-based polyols by using a filler. These examples are not meant in anyway to limit the scope of this invention.

EXAMPLE 20

A cast polyurethane resin containing silica filler was made from 40 parts of soy polyol, the product of Example 9, 20 parts of Isonate 2143L, 2 parts of drying agent, 0.4 parts of antifoaming agent, and 60 parts of silica filler. Silica having an average particle size of 6.5 microns was used.

The silica was dried for 20 hours at 110° C. The soy polyol, drying agent and antifoaming agent were mixed together to form a polyol component. This polyol component was dried for 20 hours at 110° C. The polyol component was mixed with the silica while still hot. These components were stirred for 2 minutes and then placed under vacuum at 60° C. for 5 minutes until foaming stopped. Next, Isonate 2143L was added at 60° C. The polyol and the isocyanate components were stirred under nitrogen for 2 minutes and then under vacuum for 5 minutes at 60° C. until the foaming stopped. The mixture was then poured into a mold under nitrogen and the unit was left under vacuum to evacuate bubbles (5 minutes at 60° C.) and then the vacuum was removed. The sample was baked for 24 hours at 110° C. to complete the reaction. The sample was then cooled to room temperature and demolded. This cast polyurethane resin appeared as a rigid plastic having a glass transition temperature of 75° C. The cast resin may be molded into electroinsulating components.

EXAMPLE 21

A cast polyurethane resin containing silica filler was made with 40 parts of soy polyol, the product of Example 9, 18 parts of PAPI 2901, 2 parts of drying agent, 0.4 parts of antifoaming agent, and 80 parts of silica filler.

The silica was dried for 20 hours at 110° C. The soy polyol, drying agent and antifoaming agent were mixed together to form a polyol component. This polyol component was dried for 20 hours at 110° C. The polyol component was mixed with the silica while still hot. These components were stirred for 2 minutes and then placed under vacuum at 60° C. for 5 minutes until foaming stopped. Next, PAPI 2901 was added at 60° C. The polyol and the isocyanate components were stirred under nitrogen for 2 minutes and then under vacuum for 5 minutes at 60° C. until the foaming stopped. The mixture was then poured into a mold under nitrogen and the unit was left under vacuum to evacuate bubbles (5 minutes at 60° C.) and then the vacuum was removed. The sample was baked for 24 hours at 110° C. to complete the reaction. The sample was then cooled to room temperature and demolded. This cast polyurethane resin appeared as a rigid plastic having a glass transition temperature of 80° C. The cast resin may be molded into electroinsulating components.

From the foregoing, it will be seen that this invention is one well adapted to attain all the ends and objects hereinabove set forth together with other advantages which are obvious and inherent to the structure. It will be understood that certain features and subcombinations are of utility and may be employed without reference to other features and subcombinations. This is contemplated by and is within the scope of the claims. Since many possible embodiments may be made of the invention without departing from the scope thereof, it is to be understood that all matter herein set forth is to be interpreted as illustrative and not in a limiting sense.

We claim:

1. A method for making a vegetable oil-based polyol from vegetable oil, comprising:
   (a) adding a peroxyacid to vegetable oil wherein said peroxyacid and said vegetable oil react to form an epoxidized vegetable oil; and
   (b) adding said epoxidized vegetable oil directly from step (a) without intermediate purification to a mixture of an alcohol, water, and fluoboric acid wherein said epoxidized vegetable oil reacts with said mixture to form a vegetable oil-based polyol.

2. The method of claim 1, wherein said peroxyacid is selected from the group consisting of m-chloroperbenzoic acid and peracetic acid.

3. The method of claim 2, wherein said alcohol is a mixture of methanol and isopropanol.

4. The method of claim 1, wherein said peroxyacid is added to said vegetable oil in a dropwise fashion, said vegetable oil and said peroxyacid are stirred so as to react to form epoxidized vegetable oil, said epoxidized vegetable oil is added dropwise to said mixture, and said mixture and said epoxidized vegetable oil are stirred wherein a vegetable oil-based polyol forms.

5. The method of claim 1, wherein said peroxyacid is in a solvent, said epoxidized vegetable oil is formed in said solvent, and said epoxidized vegetable oil in said solvent is added to said mixture.

6. The method of claim 5, wherein said solvent is selected from the group consisting of acetic acid, formic acid, and chloroform.

7. A method of making a vegetable oil-based polyol from epoxidized vegetable oil, comprising:
   hydroxylating epoxidized vegetable oil with a catalytic amount of fluoboric acid, an alcohol, and water.

8. The method of claim 7, wherein said epoxidized vegetable oil has about 2 to 6 epoxy groups per molecule.

9. The method of claim 8, wherein the molar ratio of said water to said epoxy groups is at least about 1:1.

10. The method of claim 7, wherein said alcohol is a mixture of methanol and isopropanol.

11. The method of claim 8, wherein the molar ratio of said alcohol to said epoxy groups is at least about 1:1.

* * * * *